(12) United States Patent
Whittum et al.

(10) Patent No.: US 8,198,587 B2
(45) Date of Patent: Jun. 12, 2012

(54) COMPACT, INTERLEAVED RADIATION SOURCES

(75) Inventors: David Whittum, Sunnyvale, CA (US); James E. Clayton, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 560 days.

(21) Appl. No.: 12/313,752

(22) Filed: Nov. 24, 2008

(65) Prior Publication Data
US 2010/0127169 A1   May 27, 2010

(51) Int. Cl.
*G01N 23/00* (2006.01)
(52) U.S. Cl. ........ 250/306; 250/307; 250/310; 250/311; 250/493.1; 250/492.1
(58) Field of Classification Search .................. 250/306, 250/307, 492.1, 492.3, 396 R, 396 ML; 378/57, 378/67, 137
See application file for complete search history.

(56) References Cited

U.S. PATENT DOCUMENTS

| | | | |
|---|---|---|---|
| 3,379,911 A | | 4/1968 | Enge |
| 3,867,635 A | * | 2/1975 | Brown et al. ............. 250/396 R |
| 3,965,434 A | | 6/1976 | Helgesson |
| 4,322,622 A | | 3/1982 | Tronc |
| 4,382,208 A | | 5/1983 | Meddaugh et al. |
| 4,389,572 A | * | 6/1983 | Hutcheon ................ 250/396 R |
| 4,400,650 A | | 8/1983 | Giebeler, Jr. |
| 4,425,506 A | * | 1/1984 | Brown et al. .......... 250/396 ML |
| 4,726,046 A | | 2/1988 | Nunan |
| 5,495,106 A | | 2/1996 | Mastny |
| 5,524,133 A | | 6/1996 | Neale et al. |
| 5,638,420 A | | 6/1997 | Armistead |
| 5,757,146 A | | 5/1998 | Carder |
| 5,784,430 A | | 7/1998 | Sredniawski |
| 5,809,106 A | | 9/1998 | Kitade et al. |

(Continued)

FOREIGN PATENT DOCUMENTS

WO    WO 01/27601 A1    4/2001
(Continued)

OTHER PUBLICATIONS

Xiang et al; "A Portable X-Band On-Axis Standing Wave Linac Structure", Proceedings of the 17th 1997 IEEE Particle Accelerator Conference. May 12-16, 1997 p. 1221-1223; Vancouver, British Columbia, Canada. Available at t http://epaper.kek.jp/pac97/papers/pdf/9W036.PDF.

(Continued)

*Primary Examiner* — Michael Maskell
(74) *Attorney, Agent, or Firm* — Brandon N. Sklar, Esq.; Kaye Scholer LLP

(57) ABSTRACT

Compact, dual energy radiation scanning systems are described comprising two particle beam accelerators, each configured to accelerate charged particles to different energies, positioned parallel to a direction of movement of an object to be inspected. The accelerator may be positioned perpendicular to a plane of the conveying system, instead. Bend magnet systems bend each charged particle beam toward a respective target. Alternatively, a single dual energy accelerator capable of accelerating charged particles to at least two different energies is positioned parallel to the direction of movement of the object, or perpendicular to a plane of the conveying system. A single bend magnet system is provided to bend each accelerated charged particle beam toward the same target. The particle beams may be bent through an orbit chamber. Two separate passages may be defined through at least part of the orbit chamber, one for charged particles having each energy.

25 Claims, 12 Drawing Sheets

U.S. PATENT DOCUMENTS

| | | | |
|---|---|---|---|
| 5,848,115 | A | 12/1998 | Little et al. |
| 5,917,880 | A | 6/1999 | Bjorkholm |
| 6,366,021 | B1 | 4/2002 | Meddaugh et al. |
| 6,445,766 | B1 * | 9/2002 | Whitham .................. 378/65 |
| 6,453,007 | B2 | 9/2002 | Adams et al. |
| 6,580,940 | B2 | 6/2003 | Gutman |
| 6,628,745 | B1 | 9/2003 | Annis et al. |
| 6,778,633 | B1 | 8/2004 | Loxley et al. |
| 6,813,336 | B1 | 11/2004 | Siochi |
| 6,844,689 | B1 | 1/2005 | Brown et al. |
| 6,864,633 | B2 | 3/2005 | Trail et al. |
| 6,954,515 | B2 * | 10/2005 | Bjorkholm et al. ......... 378/137 |
| 7,130,371 | B2 | 10/2006 | Elyan et al. |
| 7,162,005 | B2 | 1/2007 | Bjorkholm |
| 7,242,742 | B2 | 7/2007 | Calderon et al. |
| 7,257,188 | B2 | 8/2007 | Bjorkholm |
| 7,639,785 | B2 * | 12/2009 | Kirshner et al. ............ 378/137 |
| 7,646,851 | B2 * | 1/2010 | Liu et al. .................... 378/98.9 |
| 7,786,823 | B2 | 8/2010 | Heisen et al. |
| 2002/0154734 | A1 | 10/2002 | Reim |
| 2004/0057554 | A1 | 3/2004 | Bjorkholm |
| 2006/0008052 | A1 * | 1/2006 | Elyan et al. ................ 378/57 |
| 2007/0018117 | A1 * | 1/2007 | Calderon et al. ........... 250/492.1 |
| 2007/0296530 | A1 | 12/2007 | Heisen et al. |
| 2008/0014643 | A1 * | 1/2008 | Bjorkholm .................. 436/57 |
| 2010/0038563 | A1 | 2/2010 | Chen et al. |
| 2010/0039051 | A1 | 2/2010 | Clayton et al. |

FOREIGN PATENT DOCUMENTS

| | | | |
|---|---|---|---|
| WO | WO 2008/048246 A2 | 4/2008 | |

OTHER PUBLICATIONS

Enge, Harold A., "Achromatic Magnetic Mirror for Ion Beams", The Review of Scientific Instruments, vol. 34, No. 4, pp. 385-390, Apr. 1963.

Sarfehnia et al.; "Beam characterization of orthogonal bremsstrahlung photons for high contrast verification imaging", Canadian Medical Phycis Newsletter; pp. 10-19; Jan. 2007.

G. Chen et al,"Dual Energy X-ray radiography for automatic high-Z material detection," Nuclear Instruments and Methods in Physics Research B, vol. 261 (2007), pp. 356-359.

Varian Medical Systems, Inc; "Linatron—M Modular high-energy X-ray source"; Security & Inspection Products; Available at http://www.varian.com/media/security_and_inspection/products/pdf/cargobriefpdf; Sep. 2007.

Varian Medical Systems, Inc; "Linatron—Mi Modular interlaced high-energy X-ray source"; Security & Inspection Products; Available at http://www.varian.com/media/security_and_inspection/products/pdf/SIPspecMI4.pdf; Jan. 2007.

Wang, Xue-Wu et al., "Material Discrimination by High-Energy X-Ray Dual-Energy Imaging"; High Energy Physics and Nuclear Physics, vol. 31 No. 11, Nov. 2007, pp. 1076-1081.

Gongyin Chen; "Understanding X-ray cargo imaging"; Nuclear Instruments and Methods in Physics Research B; Science Direct; Available online Aug. 19, 2005.

International Search Report from PCT/US09/006262, 2009.

Written Opinion of the International Searching Authority from PCT/US09/006262, 2009.

* cited by examiner

COMPACT, INTERLEAVED RADIATION SOURCES

FIELD OF THE INVENTION

Radiation sources and radiation scanning systems, and more particularly, X-ray radiation sources emitting radiation transverse to a longitudinal axis of the source and X-ray scanning systems using such sources for examining the contents of an object, for example.

BACKGROUND OF THE INVENTION

Radiation is commonly used in the non-invasive inspection of objects such as luggage, bags, briefcases, and the like, to identify hidden contraband at airports and public buildings. The contraband may include hidden guns, knives, explosive devices and illegal drugs, for example.

FIG. 1 is a front view of an example of an X-ray scanning system 10, referred to as a line scanner, for scanning luggage in airports, for example. The object 12 to be inspected is conveyed through a shielded tunnel 13 between a stationary source of radiation 14, such as X-ray radiation, and a stationary detector array 16, by a conveying system 18. The source 14 is typically a source of X-ray radiation of about 160 KeV to about 450 KeV. The source may be an X-ray tube, for example. The radiation is collimated into a fan beam 20 that intercepts the entire height of the object 12. Windows 21a, 21b are provided in the walls of the tunnel 13 to allow for the passage of radiation to the object 12 from the source 14 and from the object to the detector array 16. The detector array 16 may also be provided within the shielded tunnel 13, in which case only one window 21a would be required. The conveyor system 18 may comprise a mechanically driven belt comprising material that causes low attenuation of the radiation. The conveyor system 18 can also comprise mechanically driven rollers, with gaps in the rollers to allow for the passage of the radiation. Shielding walls 22 surround the source 14, the detector 16 and a portion of the conveying system 18. Openings (not shown) are provided in the shielding walls 22 for the object to be conveyed into and out of the scanning system 10 by the conveying system 18. Such systems are generally large. In another example, the object may be stationary and the radiation source and detector may be moved past the object by a suitable conveying system.

Radiation transmitted through the object 12 is attenuated to varying degrees by the object and its contents. The attenuation of the radiation is a function of the amount (thickness) and atomic composition of the materials through which the radiation beam passes. The attenuated radiation is detected and radiographic images of the contents of the object 12 are generated for inspection. The images show the shape, size and varying densities of the contents.

Standard cargo containers are typically 20-50 feet long (6.1-15.2 meters), 8 feet high (2.4 meters) and 6-9 feet wide (1.8-2.7 meters). Air cargo containers, which are used to contain plural pieces of luggage or other objects to be stored in the body of an airplane, may range in size from about 35×21×21 inches (0.89×0.53×0.53 meters) up to about 240× 96×118 inches (6.1×2.4×3.0 meters). Large collections of objects, such as many pieces of luggage, may also be supported on a pallet. Pallets, which may have supporting sidewalls, may be of comparable sizes as cargo containers. The term "cargo conveyance" is used herein to refer to both cargo containers and pallets. The low energies used in typical X-ray luggage and bag scanners, described above (160 KeV-450 KeV), are too low to penetrate through the much larger cargo containers or collections of objects. In addition, many such systems are too slow to economically inspect larger objects, such as cargo containers.

To penetrate larger cargo containers, X-ray radiation of at least about 1 MeV range is generally required. Linear accelerators may be used to generate X-ray radiation in the MeV range. The actual size may depend on the frequency band of the accelerator and the amount of shielding, which is dependent on the energy and flux of the generated radiation, as well as the expected locations of people and the amount of time those people may be exposed to radiation. Typical X-ray scanning system used to screen cargo containers have lengths ranging from about 1 meter to about 5 meters for 3-4 MeV system, and up to about 3.3 meters for a 5-15 MeV system. In addition, the intensity of the radiation is greatest in a forward direction, along the longitudinal axis of the electron beam. The uniformity of the emitted radiation decreases as the angle from the forward direction is increased. To maintain dose rate uniformity, at peak X-ray energy of about 9 MeV, for example, a narrow beam having a total arc of up to about 30 degrees tends to be used. At a peak energy of about 3 MeV, a beam having an arc up to about 65-70 degrees may be used. The smaller the arc, the farther the source must be in order to intercept the entire object. The length of the high energy X-ray sources and the beam arc tend to make higher energy X-ray scanning systems large. At these high energies, more shielding is also generally required.

It has been found to be difficult to distinguish nuclear devices and nuclear materials from other dense or thick items that may be contained within the object by standard X-ray scanning. The information that may be derived about the material type of the contents of objects by X-ray scanning may be enhanced by the use of radiation beams in the MeV energy range, with two or more different energy spectra that interact differently with the material contents of the object. For example, the attenuation of a 6 MeV X-ray radiation beam by the contents of the object will be different from the attenuation a 9 MeV X-ray radiation beam by the same contents, due to the differing effects of Compton Scattering and induced pair production on the different energy beams. A ratio of the attenuations at the two X-ray energies may be indicative of the atomic numbers of the material through which the radiation beam passes, as described in U.S. Pat. No. 5,524,133, for example, which is incorporated by reference herein. More sophisticated dual energy analysis techniques are described in U.S. Pat. No. 7,257,188, for example, which is assigned to the assignee of the present invention and incorporated by reference herein. Ratios of high and low energy attenuations may also be plotted against object thickness to facilitate material identification, as described in "Dual Energy X-ray radiography for automatic high-Z material detection," G. Chen et al, NIM (B), Volume 261 (2007), pp. 356-359, which is also incorporated by reference herein.

SUMMARY OF THE INVENTION

Since the space occupied by an X-ray scanning system could often be used for other important purposes, a more compact X-ray scanning system would be advantageous.

In accordance with an embodiment of the invention, a radiation scanning system to examine contents of objects is disclosed comprising first and second radiation sources, each comprising first and second respective sources of charged particles coupled to first and second respective accelerators. The first and second accelerators each accelerate the first and second charged particles to a first and second energies, respectively. The radiation sources further comprise first and second respective targets. A first bend magnet is positioned to receive the accelerated first charged particles along a first axis from the first accelerator and to direct the charged particles toward the first target along a second axis different from the first axis. A second bend magnet is positioned to receive the second accelerated charged particles from the second accelerator along a third axis and to direct the charged particles toward the second target along a fourth axis different from the fourth axis. Impact of the first and second accelerated charged particles on the first and second targets, respectively, causes generation of radiation having first and second energies, respectively. At least one detector is positioned to detect radiation after interacting with the object. The system further comprises a support to support an object to be scanned. The support may be part of a conveyor system to move the object through the first and second radiation beams during scanning. The system may further comprise a conveyor system to move at least one of the at least one detector and the radiation sources past the object. In other words, the conveyor system may move the radiation sources and/or the at least one detector. The first and second radiation sources may be the same.

The first and second targets may be positioned on a first side of the conveyor system and the at least one detector may be positioned on a second side of the conveyor system opposite the first side. The at least one detector may comprise a first detector aligned with the first radiation source and a second detector different than the first detector, aligned with the second radiation source. The first radiation beam and the second radiation beams may comprise X rays. The charged particles may comprise electrons.

A processor may be coupled to the first and second radiation sources. The processor may be configured to selectively activate the first source or the second source to selectively cause generation of the first radiation beam from the first radiation source or the second radiation beam from the second radiation source. The processor may be configured to implement a first predetermined radiation pulse pattern and to change the first predetermined radiation pulse pattern to a second predetermined radiation pulse pattern different than the first radiation pulse pattern based, at least in part, on the radiation detected at at least one of the energies during execution of the first predetermined radiation pulse pattern. The processor may also be configured to cause operation of the conveyor system at a first speed during scanning and change the first speed to a second, different speed during scanning, based, at least in part, on the radiation detected at at least one of the energies while scanning at the first speed.

The first radiation beam and the second radiation beam may each have energies of at least 1 MeV. The first radiation beam may have an energy of 6 MeV and the second radiation beam may have an energy of 9 MeV.

The first and second bend magnets each comprise stepped-field bend magnets or Enge magnets, for example. The first and second bend magnets may be configured to bend the first and second charged particles 270°.

In accordance with another embodiment, a method of generating radiation is disclosed comprising accelerating first charged particles to a first energy, bending the first charged particles toward a first target, generating radiation having a second energy from impact of the first charged particles on the target, accelerating second charged particles to a third energy different than the first energy, bending the second charged particles toward a second target, and generating radiation having a fourth energy different from the second energy from impact of the second charged particles on the target.

The method may comprise accelerating the first and second charged particles by a single accelerator, bending the first and second accelerated charged particles toward the same target by a single magnet, and generating radiation having the second and fourth energies from impact of the first and second accelerated charged particle beams on the same target. The method may comprise accelerating the first and second charged particles by first and second, separate, accelerators, and bending the first and second charged particles by first and second, different magnet systems.

The first and second charged particles may be bent by 270 degrees. The first and second charged particles may be bent by a varying magnetic field, or the first and second charged particles may be bent by a first and second, different magnetic fields. The first and second charged particle beams may be bent around respective, different, radii through an orbit chamber defining at least partially separate passages through the orbit chamber, for each charged particle beam.

In accordance with another embodiment, a radiation scanning system to examine contents of objects is disclosed comprising a source of charged particles, a charged particle accelerator having an input coupled to the source of charged particles to receive the charged particles, and an output to allow accelerated charged particles to exit the accelerator along a first axis. The charged particle accelerator is configured to generate a first beam of accelerated charged particles having a first energy and a second beam of accelerated charged particles having a second energy different than the first energy. A target is positioned along a second axis different than the first axis and a magnet system is provided along the axis, configured to deflect the first and second accelerated charged particles along the second axis, toward the target. Impact of the first charged particle beam on the target causes generation of a first radiation beam having a first energy and impact of the second accelerated charged particle beam on the target causes generation of a second radiation beam having a second energy different than the first energy. A support is provided to support an object for scanning. A detector is provided to detect radiation after interacting with the object. The charged particle source may comprise a source of electrons and impact of the first and second charged particle beams on the target may cause generation of X-ray radiation. The support may be part of a conveyor system to move the object through the first and second radiation beams, during scanning. A conveyor system may be provided to move the source and the detector past the object during scanning.

The radiation source may be on a first side of the conveyor system and the detector may be on a second side of the conveyor system opposite to the first side, to detect radiation transmitted through the object. The first and second axes may be transverse and the magnet system may be configured to deflect the first and second charged particle beams 270 degrees, from the first axis to the second axis.

The magnet system may further comprise an orbit chamber defining an inlet, an outlet, and a passage coupling the inlet to the outlet. The passage is configured to allow passage of the first accelerated charged particle beam and the second accelerated charged particle beam from the inlet to the outlet.

The orbit chamber may further define a wall in a portion of the passage separating a portion of the first passage from a portion of the second passage, to define separate partial passages for the first charged particle beam and the second charged particle beam. The wall may extend from a portion of the passage proximate the inlet to a portion of the passage proximate the outlet.

The orbit chamber may define a first, wider portion of each passage upstream of a second, narrower portion of each chamber. A wall transverse to the passages defines a step between the first and second portions.

In accordance with another embodiment of the invention, a method of conducting radiation scanning of an object is disclosed, comprising scanning an object with a first radiation beam pulse pattern comprising at least one of at least two different radiation beams each having a different characteristic, detecting the radiation, and analyzing the radiation detected during at the first pulse sequence. The method further comprises scanning the object with a second radiation beam pulse pattern, if suspect material is at least potentially identified, and analyzing the radiation detected during at the second pulse sequence.

Reference to the "energy" of a radiation beam refers to an energy characteristic of the radiation beam. The characteristic may be the nominal energy, average energy, or energy end point (peak energy) of the beam, for example. The term may encompass other characterizations of the energy of the beam, as well.

DETAILED DESCRIPTION OF PREFERRED EMBODIMENTS

Figure 2:
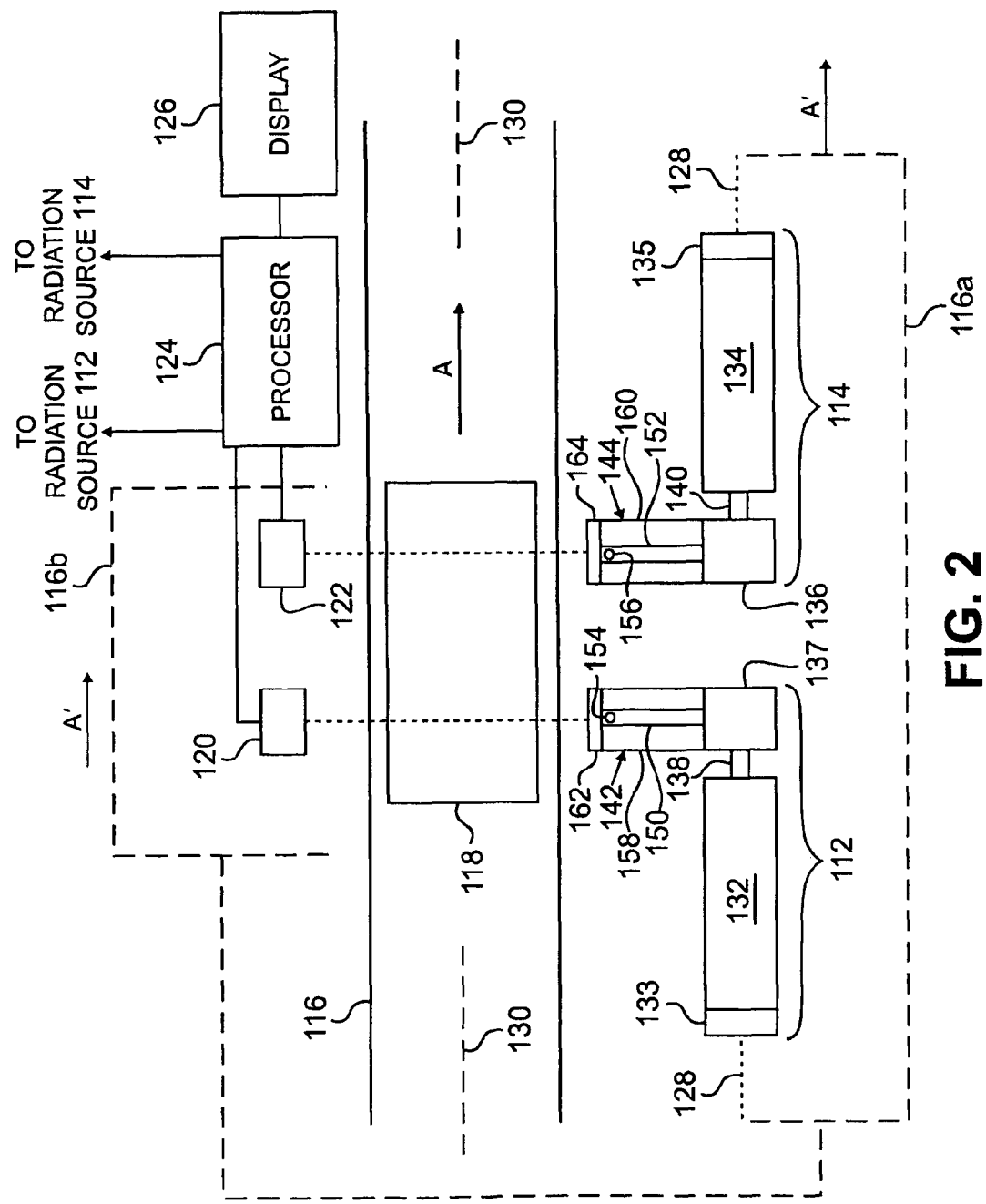
FIG. 2 is a schematic representation of a top view of a dual energy radiation scanning system in accordance with an embodiment of the invention, comprising first and second radiation sources.

FIG. 2 is a schematic representation of a top view of a dual energy radiation scanning system 100 in accordance with an embodiment of the invention, comprising a first radiation source 112 and a second radiation source 114, adjacent to a support 116 for the object 118. In this example, the support 116 is a conveyor that moves the object 118, such as a cargo conveyance, in a direction A along an axis 130, past the radiation sources 112, 114. The conveyor 116 includes a flat surface 117 that supports the cargo conveyance 118. The radiation sources 112, 114 may be configured to generate fan beams or cone beams, for example, through which the object 118 is moved. Detectors 120, 122 are provided on an opposite side of the conveyor 116 than the radiation sources 112, 114. The detectors 120, 122 are aligned with the sources 112, 114, to detect radiation passing through the cargo conveyance 118. The detectors 120, 122 are coupled to a processor 124 and a display 126. The processor 124, or another processor, may be coupled to the radiation sources 112, 114, and to the conveyor 116a, 116b, 116c to control their operation, as well. The detectors 120, 122 may be detector arrays, for example. Additional circuitry, such as analog-to-digital circuitry, may be provided between the detectors 120, 122 and the processor 124, as is known in the art.

In an alternative configuration, the support 116 is a platform, the radiation sources 112, 114 are supported by a conveyor 116 (indicated in phantom in FIG. 2), and the detectors 120, 122 are supported by another (or the same) conveyor system 116b, also shown in phantom. The conveyors 116a, 116b move the radiation sources 112, 114 and the detectors 120, 122 past the stationary object 118 in the direction A'. The radiation beams emitted by the sources 112, 114 toward the object 118 are then moved through the object. Conveying systems that move a radiation source and/or a detector past a container during scanning are known in the art. A straddle type system for moving both a source and a detector past a container is described in U.S. Pat. No. 5,638,420, which is incorporated by reference herein.

Figure 1:
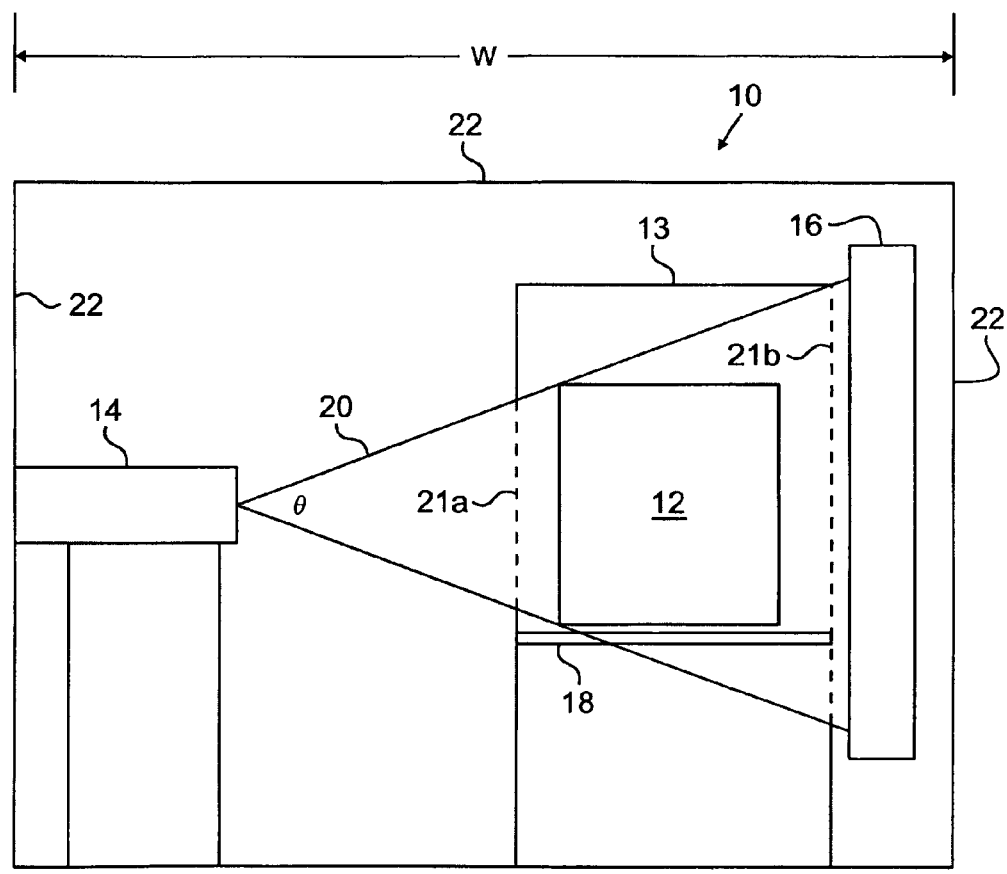
FIG. 1 is a front view of an example of a prior art X-ray scanning system, referred to as a line scanner, for scanning luggage in airports.

In this example, the radiation sources 112, 114 are linear accelerators arranged horizontally, with their longitudinal axes parallel to an axis 130 of the conveyer system 116, to provide a more compact system than if the linear accelerators were perpendicular to the direction of movement of the conveying system 116 or the conveying systems 116a, 116b, as in the system 10 of FIG. 1. The longitudinal axes of each linear accelerator may be aligned with the same axis 128 or different axes parallel to the axis 130. Instead of being parallel to the directions of movement A, A', the long axes of the linear accelerators may also be transverse to the directions of movement, but not perpendicular to the directions of movement A, A', to provide a more compact system than if the accelerators were perpendicular, even if not as compact as the configuration of FIG. 2.

The first and second linear accelerators 112, 114 each comprise a respective accelerator 132, 134, to accelerate charged particles, such as electrons, to different nominal energies, as is known in the art. The charged particles are provided by charged particle sources 133, 135, such as electron guns, for example.

The accelerated charged particles output from each of the accelerators 132, 134 may be coupled to bend magnet systems 136, 137 through drift tubes 138, 140, respectively. The accelerators 132, 134, bend magnet systems 136, 137, and drift tubes 138, 140 are under vacuum, as is known in the art. Drift tubes 150, 152 are provided at the output of the bend magnet systems 136, 137, to couple the bend magnet systems to target assemblies 142, 144, and to the targets 154, 156, respectively. The drift tubes 150, 152 and the target assemblies 142, 144 are also under vacuum.

The target assemblies 142, 144 comprise targets 154, 156, such as tungsten, for example, as is known in the art. Shielding material 158, 160 surrounds the drift tubes 150, 152 and targets 154, 156. Collimators 162, 164 may be provided downstream of each target assembly 142, 144, respectively, to shape the radiation beam emitted by the targets 154, 156. Each radiation beam may be collimated into a fan beam or a cone beam, for example.

The radiation sources 112, 114 may be sources of X-ray radiation, for example. The nominal electron energies of the radiation sources 12, 14 may be 9 MeV and 6 MeV respectively, for generating X-ray beams having energies of 9 MV and 6 MV, respectively. 9 MV and 6 MV X-ray radiation beams are appropriate for scanning cargo conveyances, such as cargo containers having a thickness of 6 feet (1.8 m) or more, for example. Other nominal electron energies for generating other X-ray energies, to scan cargo conveyances or for other applications, may be provided. For example, nominal electron energies of the radiation sources 112, 114 may be 6 MeV and 1 MeV, to generate nominal X-ray energies of 6 MeV and 1 MeV, or 6 MeV and 3.5 MeV, may be provided to generate X-ray energies of 6 MeV and 3.5 MeV, respectively. The dose rate of the two radiation sources in this example are the comparable.

The linear accelerators 132, 134 may each be a LINATRON® or CLINAC® available from Varian Medical Systems, Inc., Palo Alto, Calif., for example. The sources may emit pulses of charged particles, such as 360 pulses per second, or more, for example. In the Varian Linatron®, up to 500 pulses are output per second. Linear accelerators that may be used are also described in U.S. Pat. No. 6,864,633 B2, and U.S. Pat. No. 6,366,021 B1, which are assigned to the assignee of the present invention and are incorporated by reference herein.

The bend magnet systems 136, 137 may be 270° bending magnet systems 134, 136, for example. The bend magnet systems 136, 137 bend the charged particles received from the first linear accelerator 112 and the second linear accelerator 114 toward the targets 142, 144, respectively. Impact of the charged particles on the targets 142, 144 generates X-ray radiation due to the Bremmstrahlung effect, as it is known in the art. The beam of charged particles is turned 90 degrees from the axis of the accelerator, toward the target, by deflecting the beam 270 degrees by one or more magnetic fields, as is known in the art. Examples of bend magnet systems 136, 137 that may be used are described in more detail below.

In one example, the bend magnet systems 136, 137 each comprise a 270° stepped field bending magnet which is at least approximately achromatic so that it causes only a small dispersion of the charged particle beam at an output of the magnet, as is known in the art. An example of a stepped field magnet is described in U.S. Pat. No. 4,425,506 (the '506 patent), which is incorporated by reference herein. In the '506 patent, a stepped magnet subjects charged particles to at least two adjacent regions, each with a different, homogeneous magnetic field, while traversing one-half of a symmetric trajectory. The beam of charged particles is first subjected to a low magnetic field in a low magnetic field region, which causes the beam to bend around a first angle $\alpha 1$, then it enters a high magnetic field in a high magnetic field region, where it is deflected through a second angle $2\alpha 2$ ($\alpha 2$ on each side of a symmetry plane). The beam then re-enters the low magnetic field region, where it is deflected another angle $\alpha 1$, for a total bend of 270° ($2(\alpha 1+\alpha 2)$).

The ratio of the high magnetic field to low magnetic field may be about three-to-one, for example. All the pole faces are parallel, which creates intrinsic symmetries in the optical properties and facilitates manufacture.

Figure 3:
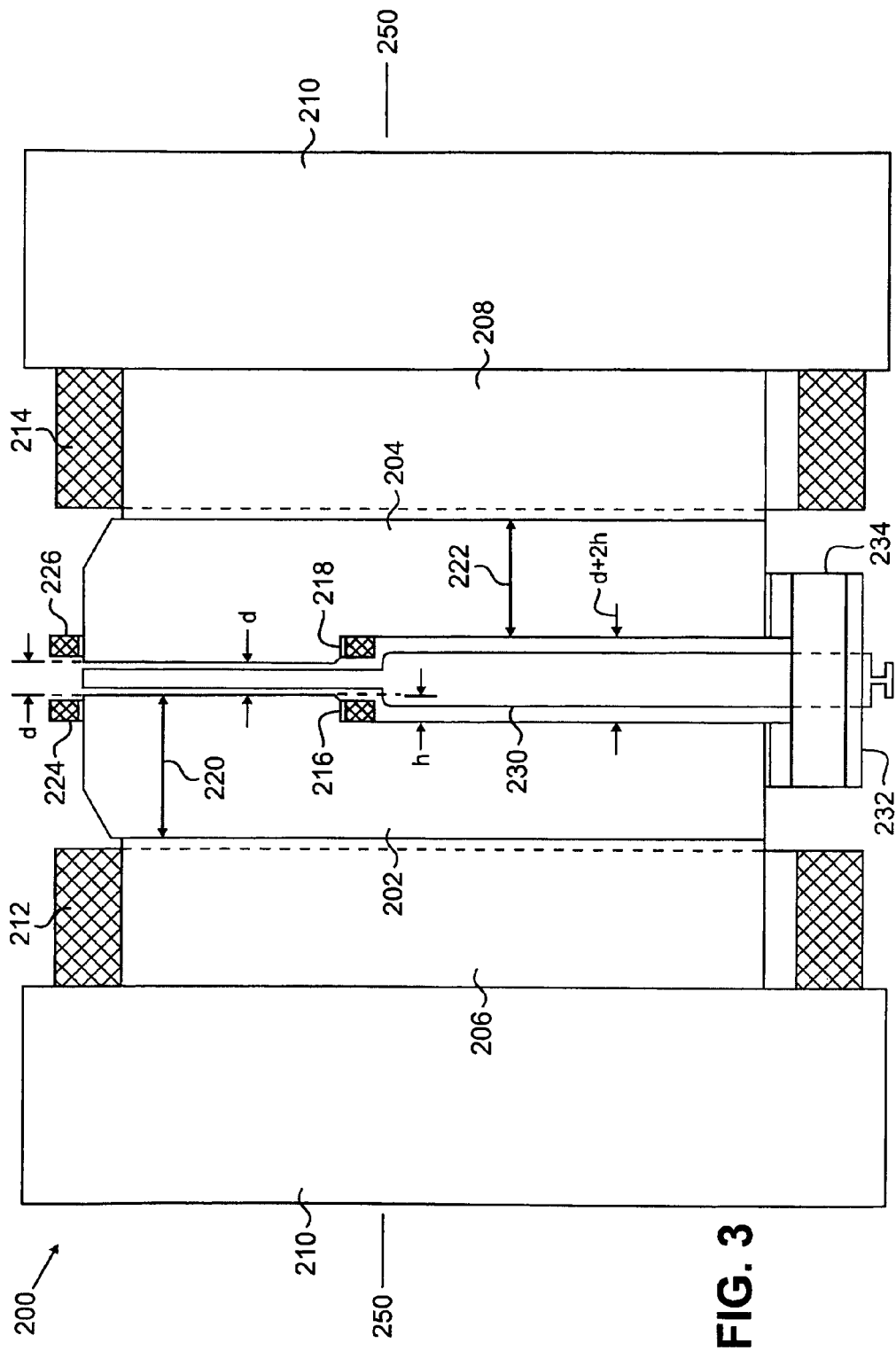
FIG. 3 shows a pole piece of an example of an electromagnet, which may be used in a bend magnet system in embodiments of the present invention.

FIG. 3 shows a pole piece 200 of an electromagnet described in the '506 patent, which may be used in embodiments of the present invention. The pole piece 200 comprises pole caps 202, 204, which are coupled to outer poles 206, 208 of the magnet. The outer poles 206, 208 are coupled to a yoke 210. Current carrying coils 212, 214 are disposed about respective outer poles 206, 208, to cause generation of the magnetic field. Steps 216, 218 divide the pole caps 202, 204 into a thicker region 220 and a thinner region 222. The thicker region 220 defines a narrower gap (d) and the thinner region 222 defines a wider gap (d+2h) between the pole caps 202, 204. The thinner region 222 defines a first, uniform, lower, magnetic field B1 on one side of a plane 250 and the thicker region 220 defines a second, uniform, higher magnetic field B2 on the other side of the plane 250. Trim coils 224, 226 provide a vernier to adjust the ratio between the high and low magnetic fields.

A vacuum envelope 230, which is a thin-walled metal vessel that defines a path for charged particles to follow as the charged particles are curved by the magnetic field, is provided between the pole caps 202, 204 of the magnet 200, partially positioned within the thicker region 220 and thinner region 222 of the pole caps. The vacuum envelope 230, also referred to as an orbit chamber in the art, is under vacuum.

Figure 4:
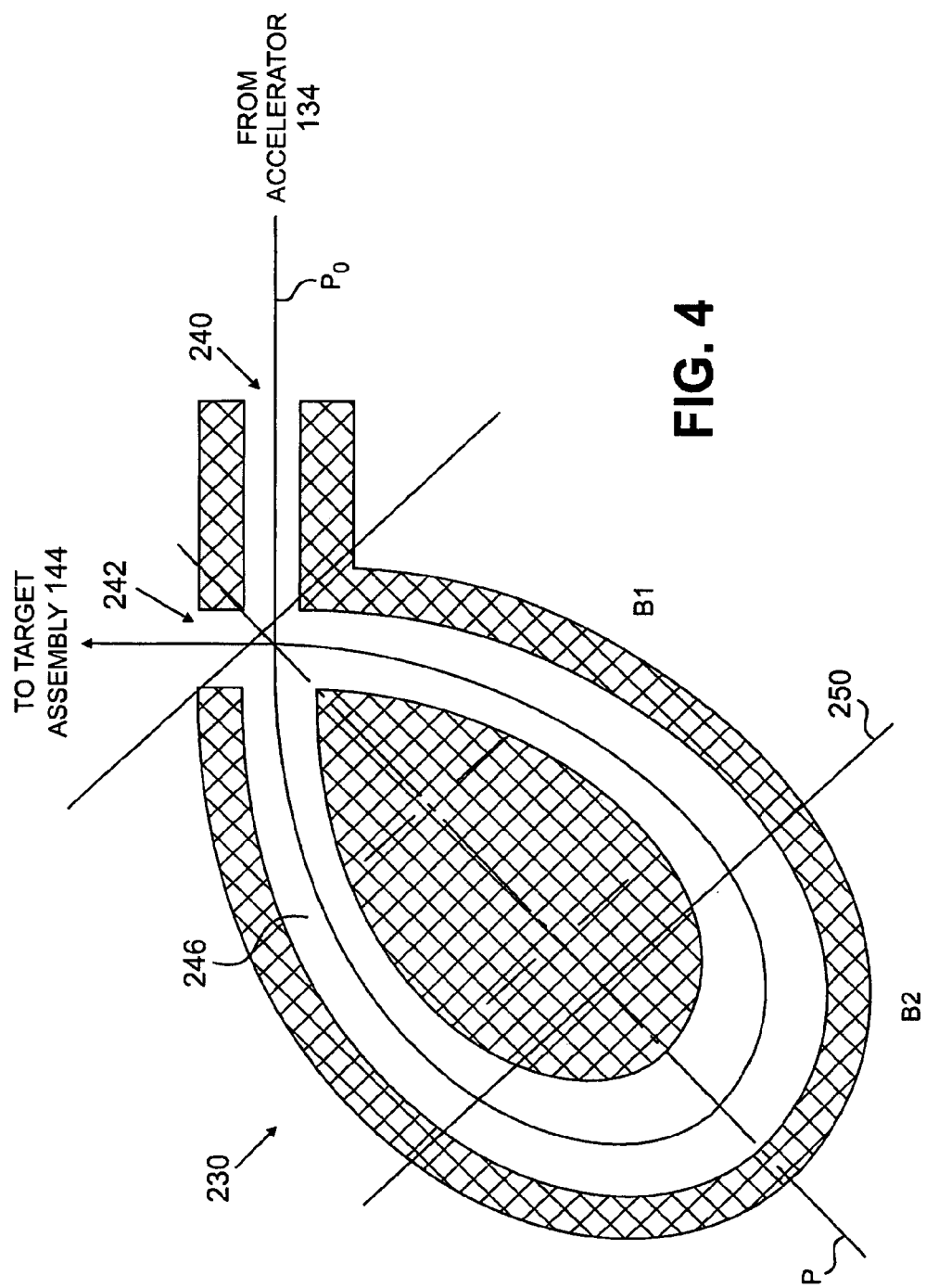
FIG. 4 is a schematic diagram of a cross-section of an example orbit chamber that may be used in the bend magnet systems in the embodiment of FIG. 1.

FIG. 4 is a schematic diagram of a cross-section of an example orbit chamber 230 that may be used in each bend magnet. The orbit chamber 230 has an inlet 240 along a first axis, an outlet 242 along a second axis perpendicular to the first axis, and a passage 246 following a curved path turning 270° to connect the inlet 240 to the outlet 242. The orbit chamber 230 may comprise oxygen-free electronic grade copper, for example, as is known in the art. The passage 246 is defined in the copper.

Figure 8:
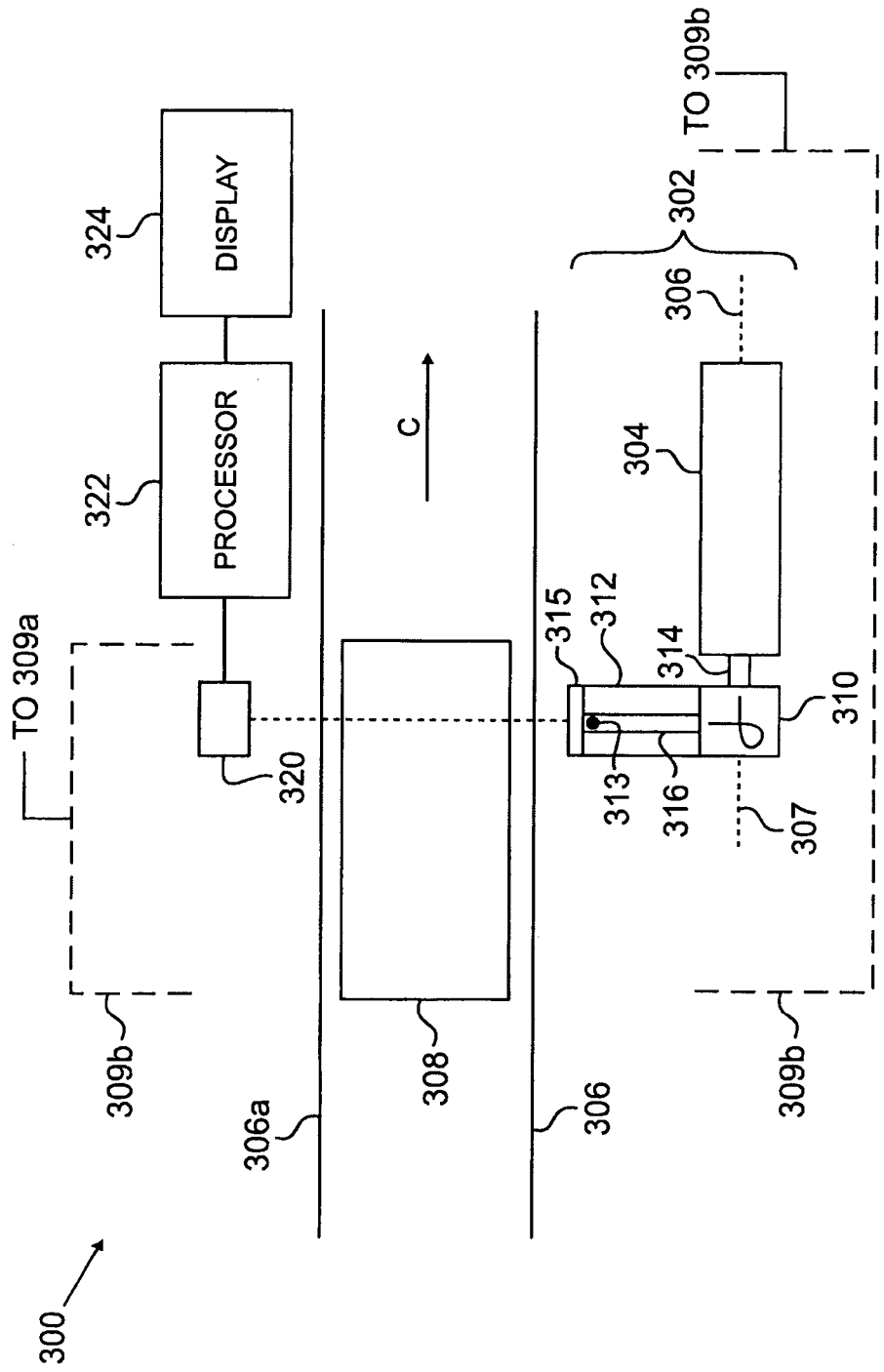
FIG. 8 is a schematic representation of another example of a dual energy radiation scanning system in accordance with an embodiment of the invention, comprising one accelerator.

The passage 246 may comprise a first, narrower portion (not shown) extending from the inlet 240 to a narrow choke or "energy slit," and a second, wider portion (not shown) extending from the choke to the outlet 242, to intercept charged particles and remove charged particles at the periphery of the beam that have been dispersed by the magnetic field. An example of a choke is shown in FIG. 8.

The orbit chamber 230 is positioned between the pole caps 202, 204 of the pole piece 200, so that a portion of the orbit chamber is within the low magnetic field region B1 defined by the thinner portion 222, and a portion of the chamber is positioned within the higher magnetic field B2 defined by the thicker portion 220. The passage 246 is perpendicular to the magnetic field, as is known in the art. Line 250 in FIG. 4 corresponds to the plane 250 in FIG. 3, between the low magnetic field region B1 and the high magnetic field region B2. A symmetry plane P of the orbit chamber 230 is indicated.

The entrances and exits of the orbit chambers 230 in the respective bend magnet systems 136, 137 are coupled to the respective drift tubes 138, 140, 150, 152, which are also under vacuum, as mentioned above.

A field clamp 232 disposed from the pole caps 202, 204 by an aluminum spacer 234 controls the fringing field at an entrance to and from the orbit chamber 230.

Ellipticity of the electron beam is generally small. However, a quadrupole (not shown) may be provided to shape the electron beam to avoid ellipticity, if desired, as is known in the art. It is noted that in cargo scanning with a fan beam or a cone beam, ellipticity may not be a concern.

Another example of an approximately achromatic beam deflection system is described in U.S. Pat. No. 3,867,635 and U.S. Pat. No. 4,322,622, which are also incorporated by reference herein.

The beam of charged particles may be deflected by a continuously spatially varying magnetic field, as well, as described, for example, in Enge, Harold A., "Achromatic Magnetic Mirror for Ion Beams," The Review of Scientific Instruments, Vol. 34, No. 4, pp. 385-390, April 1963, for example, and in U.S. Pat. No. 3,379,911 ("the '911 patent"), which are also incorporated by reference herein. In these examples, the beam enters the magnet through a pole face with an adjustable angle. For nearly the first 135° the field is homogeneous. Then the beam passes through a short region where the field has a gradient in which the magnetic field increases in intensity as a function of radius from the center. The beam then re-inters the homogeneous field and exits through another pole face with an adjustable angle. Except for the input and exit pole face angles, the system is symmetric about a 45° diagonal line through the magnet. The gradient region enables achromaticity with respect to both position and angle as long as the magnet gap is small compared to the bend radius, and the target is sufficiently distant from where the beam exits the magnet.

Figure 5:
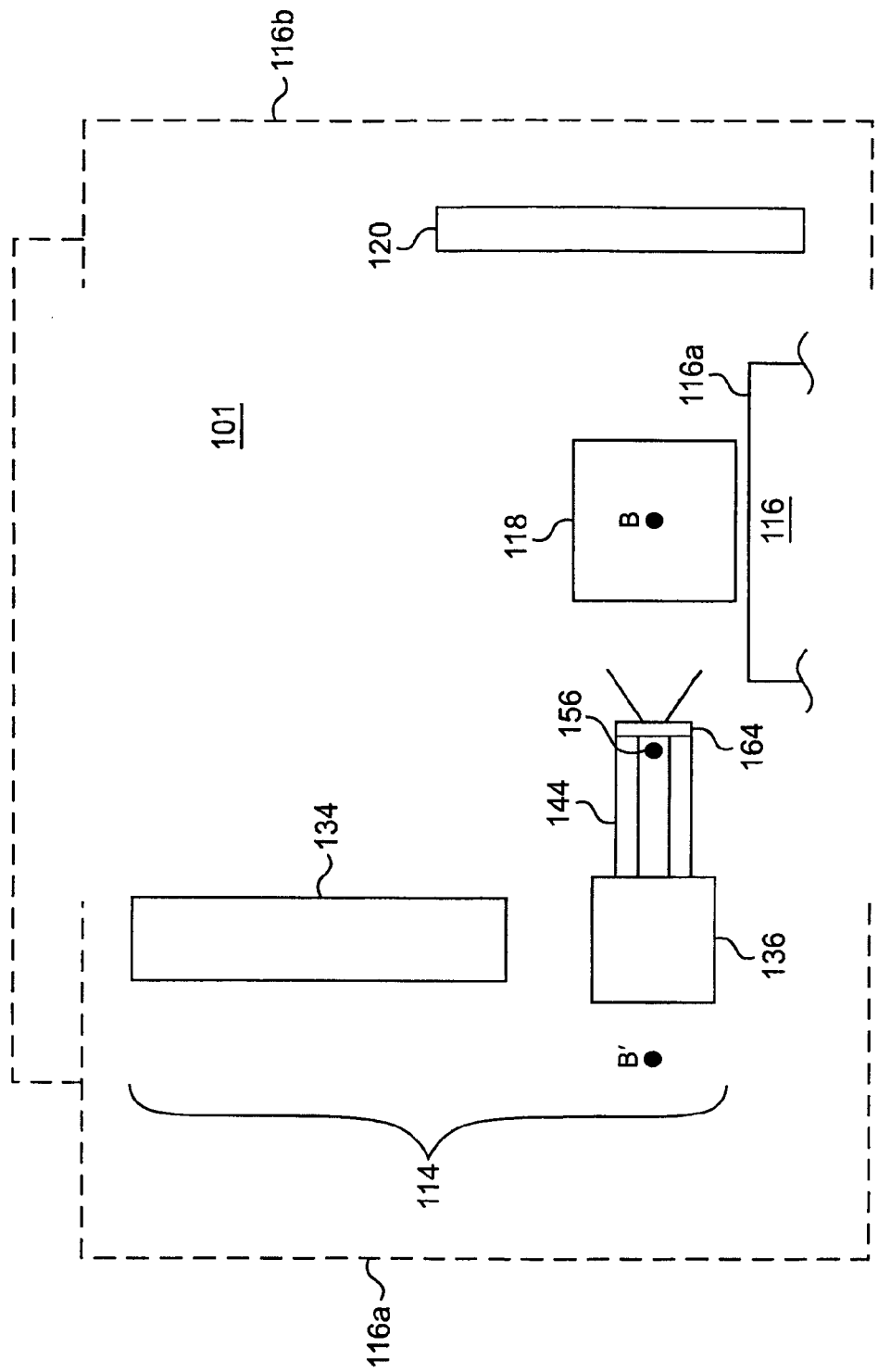
FIG. 5 is a schematic diagram of another example of the embodiment of FIG. 1, in which the accelerators are vertical.

In another example of a radiation scanning system 101 in accordance with an embodiment of the invention, the linear accelerators 132, 134 adjacent to the conveyor system 116 are vertical, and perpendicular to the direction of movement of the object 118, as shown in a side view of FIG. 5, where the object 118 is moved in a direction B out of the page by the conveyor 16 (or the radiation sources and detectors may be moved in a direction B' out of the page. A surface 116a of the conveyor 116 is perpendicular to the page and to the long axes of the accelerators 132, 134. Only the radiation source 114 is shown in this view. The linear accelerator 132 and the radiation source 112 are behind the radiation source 114 in this view and are not shown. One accelerator may be perpendicular to the direction of movement of the object 118 and one may be parallel, as well.

The processor 124 may be a logic circuit, such as an application-specific integrated circuit ("ASIC") or field programmable gate array ("FPGA"), a programmable logic controller, or a microprocessor, for example. In the systems 100, 101 of FIGS. 2 and 4, the processor 124 controls the operation of the radiation sources 112, 114 so that they generate and emit radiation pulses in a desired pattern. In one example, the pattern may comprise an alternating pattern comprising one high energy radiation pulse (9 MeV, for example) followed by one low energy radiation beam (6 MeV, for example). In another example, two high radiation pulses may be followed by two low radiation pulses followed by two high radiation pulses, etc. The pattern may also comprise different patterns of high and low radiation pulses, such as a repeating pattern of three high energy radiation pulses followed by one low energy pulse. Any pattern of radiation pulses may be generated. The detectors 120, 122 may be enabled in a corresponding pattern to detect the emitted radiation after interaction with the object 118.

The klystron 406 may be a 5.5 MW or a 3 MW S-band klystron from Communications and Power Industries, Inc., Palo Alto, Calif., for example. The rf driver 408 may be provided by Comtech PST Corp., Melville, N.Y., for example.

The accelerator 402 may be a standard S-band accelerator, such as the HE Energy CLINAC™, available from Varian Medical Systems, Inc., Palo Alto, Calif., which may be operated at either one of two energies by setting of an energy switch. The switch may be set to one of the higher or lower energies to be in optimum configuration for one of the energy settings during the interleaved operation, but not the other, or the switch may be set for an energy between the two desired energies. For example, the CLINAC™, may be set to operate at either 9 MV, 6 MV, or 7.5 MV to provide interleaved, pulsed radiation generation at 9 MeV and 6 MeV. An S-band accelerator operates in the frequency range of 2.4 GHz to 3 GHz. The accelerator 402 may also be an L-band, C-band, X-band, or K-band accelerator, instead, for example, which operate over different energy and frequency ranges. The frequency band of the klystron 406 should match the frequency band of the accelerator 402.

During operation, as the object 118 is scanned by the alternating pattern of radiation pulses from the first and second radiation sources 112, 114, the detected radiation is processed by the processor 124 for display on the display 126. Images may be displayed based on the data collected from each detector 120, 122, at each respective energy, and/or the data collected from each detector may be processed with each other and displayed. For example, dual energy images may be fused and displayed, for example.

In another example, ratios of the attenuations at the two X-ray energies, which may be indicative of the atomic numbers of the material through which the radiation beam passes, are calculated and analyzed. Ratios may be compared to tables correlating ratios with atomic numbers, as described in U.S. Pat. No. 5,524,133, for example, which is incorporated by reference herein. More sophisticated analysis of ratios from dual energy scanning may be used, such as those described in U.S. Pat. No. 7,257,188, for example, which is assigned to the assignee of the present invention and incorporated by reference herein. Ratios of high and low energy attenuations may also be plotted against object thickness to facilitate material identification, as described in "Dual Energy X-ray radiography for automatic high-Z material detection," G. Chen et al, NIM (B), Volume 261 (2007), pp. 356-359, which is also incorporated by reference herein.

In this example, the interleaving of the high and low beams at high pulse repetition frequencies of, for example, from about 500 Hz to about 2000 Hz, enables capture of two images of nearly the same object view or slice, even when the object 118 (or the radiation sources 112, 114/detector 120, 122) is moving rapidly. Comparable dose output from the two sources 112, 114 insures that both images are of comparable quality and capable of fusion for purposes of discrimination of objects of interest, such as Special Nuclear Materials.

The radiation pulse pattern can also be controlled in real time or nearly in real time based on inputs from previous frames. The processor 124, or another processor, may analyze images and/or data in real time or substantially real time via computerized algorithms, such as those described in U.S. Pat. No. 7,257,188, for example, which is assigned to the assignee of the present invention and incorporated by reference herein. If a suspect material, such as Special Nuclear Material or high density material is at least potentially identified, the pulse pattern may be changed. Computerized algorithms may analyze the probability of a certain shape having been encountered in a previous frame, and change the pulse pattern if a potentially suspect item is identified, as well.

In one example, the processor 124, or other such processor, may change the alternating radiation pulse pattern of high and low energy radiation beams from the first and second radiation sources 112, 114 to all high energy radiation beams from only the high energy radiation source (source 114, for example), if suspect material is at least potentially identified. When scanning of the suspect region is completed at the high energy, the original, alternating radiation pulse sequence, or another radiation pulse sequence, may be initiated by the processor. In another example, if analysis reveals the potential presence of a low density contraband, the processor 124 may change the alternating radiation pulse pattern to a pattern comprising only the low energy radiation pulses (6 MeV or 1 MeV, for example), from the low energy radiation source 112, for example.

If suspected Special Nuclear Material is present, a neutron detection system may be activated by the processor 124 and the presence of delayed neutrons checked for after the high energy radiation pulses, as is also described in U.S. Pat. No. 7,257,188, which is assigned to the assignee of the present invention and incorporated by reference herein.

Another radiation source (not shown) may be activated for further testing, as well. For example, a radiation source may be positioned orthogonal to the direction of the radiation beams emitted by the first and second radiation sources, and activated for further testing of a suspect region based, at least in part, on the detected radiation. A "dual view" imaging system including orthogonal radiation sources is described in U.S. patent application Ser. No. 11/485,150, filed on Jul. 12, 2006, which is assigned to the assignee of the present invention and is incorporated by reference herein.

In another example, if analysis reveals the potential presence of Special Nuclear Material, another, higher energy radiation source (not shown) may be activated to generate pulses of higher energy radiation, such as 15 MeV, to detect delayed neutrons or for other analysis to better determine whether Special Nuclear Material may be present.

The radiation pulse pattern need not be alternating. In another example, only one of the radiation sources, either the high radiation source 114 or the low radiation source 112 may be caused to generate radiation pulses by the processor 124, and if suspect material is identified, then the processor may implement an alternating pattern of high and low radiation pulses by activating both the low radiation sources 112 and the high radiation source 114 to generate radiation pulses for dual energy analysis, such as analysis of ratios, or only the high energy radiation source may be activated for a series of pulses.

Other parameters of the imaging scan may be changed automatically and in real time or nearly real time, based on the analysis of the detected radiation, as well. For example, the speed of the conveyor 116, 116a, 116b may be decreased if suspect material is potentially identified, to increase the resolution of the analysis. The conveyor 116, 116a, 116b may also be reversed to check a suspect region of the object again, optionally in accordance with another radiation pulse pattern.

Figure 6:
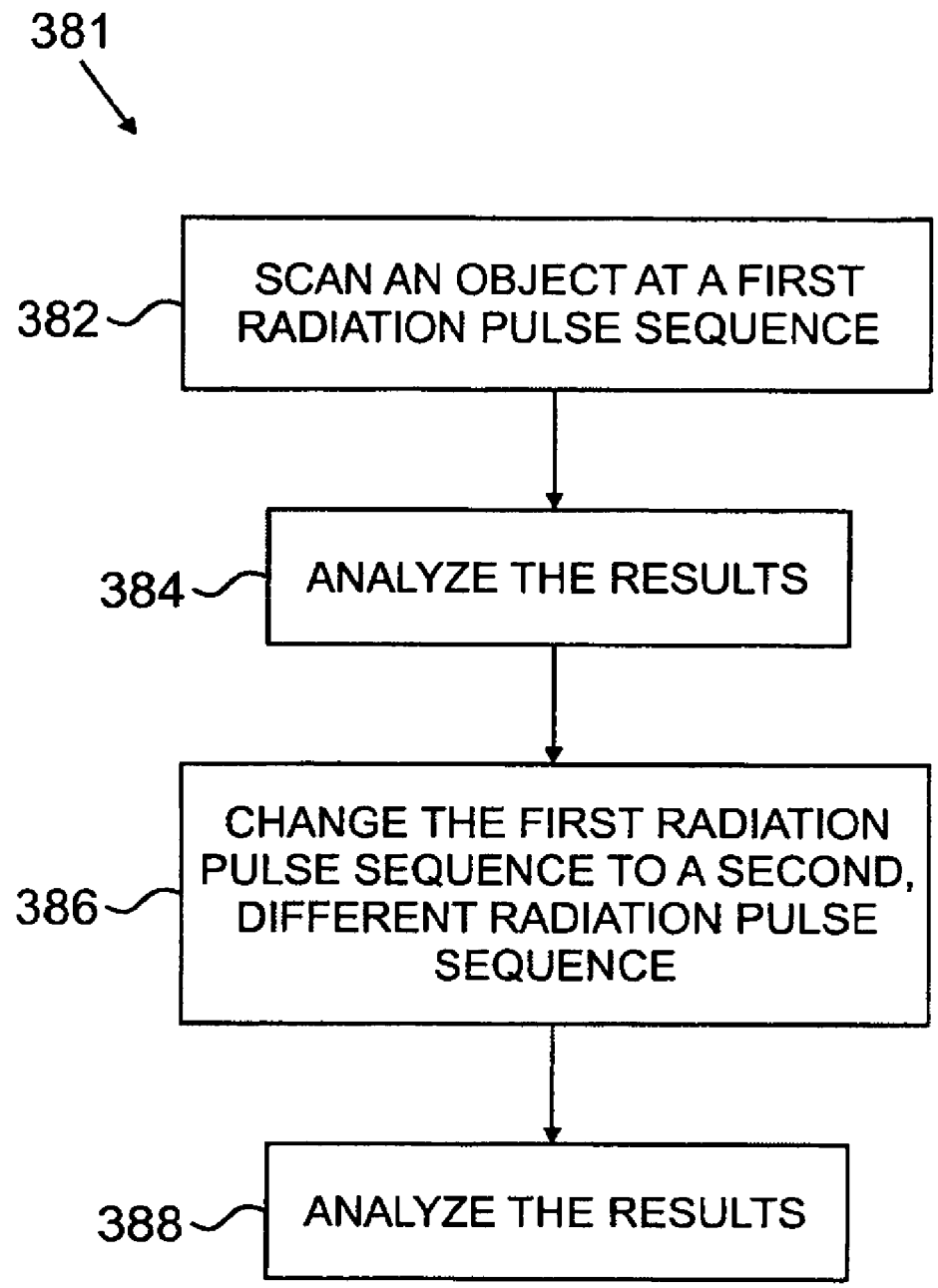
FIG. 6 is an example of a method for changing radiation pulse sequences, in accordance with an embodiment of the invention.

FIG. 6 is an example of a method 381 for changing radiation pulse sequences, in accordance with an embodiment of the invention. Scanning is conducted at a first radiation pulse pattern, in step 380. The detected radiation is analyzed, in step 382. The first radiation pulse pattern is changed to a second radiation pulse pattern based, at least in part, on the analysis, in step 384, and scanning is conducted based on the second radiation pulse pattern, in step 386. The detected radiation is analyzed in step 388.

Figure 7:
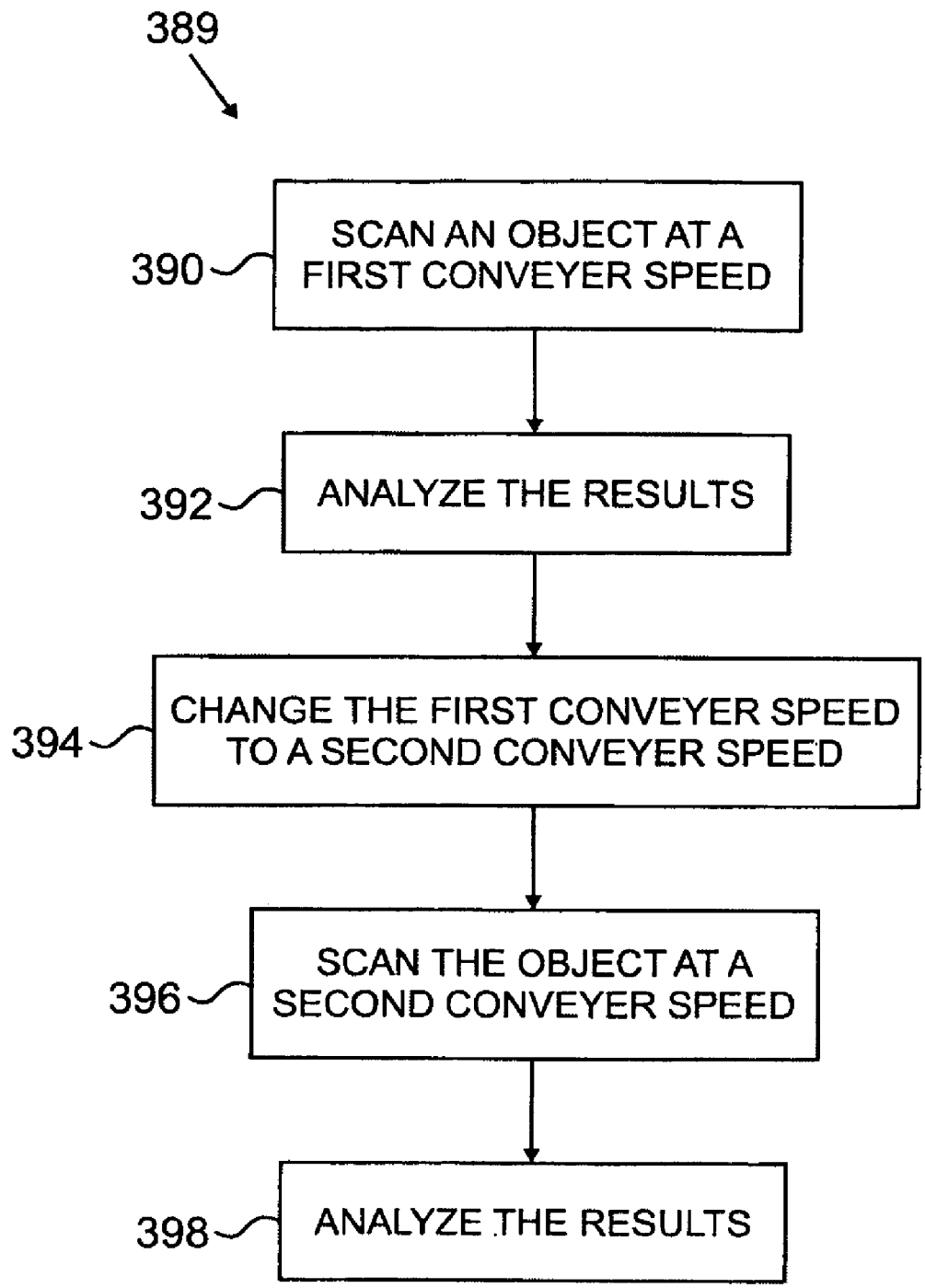
FIG. 7 is an example of a method for changing conveyor speed, in accordance with another embodiment of the invention.

FIG. 7 is an example of a method 391 for changing conveyor speed in accordance with an embodiment of the invention. An object is scanned while the conveyor 116,116a and/or 116b is moved at a first conveyor speed, in step 390. The results are analyzed in step 392. The first conveyor speed is changed to a second conveyor speed, in step 394. The object is scanned at the second conveyor speed, in step 396, and the results are analyzed, in step 398.

FIG. 8 is a schematic diagram of another example of an embodiment of a compact system 300 for examining objects with radiation at least two energies. In this example, one radiation source 302, which generates radiation at two or more energies, is positioned, horizontally, adjacent to a support 306, which may be a conveyor 306 with a surface 306a. One of the energies may be 9 MeV and the other energy may be 6 MeV, or one of the energies may be 6 MeV and the other 1 MeV, for example. In this example, the radiation beams are emitted at comparable dose rates, but that is not required. In FIG. 8, a long axis 307 of the linear accelerator 302 is parallel to the direction of movement C of the object 308 to be examined. The linear accelerator 302 may be positioned vertical and perpendicular to the direction of movement C of the object 308 and to a plane containing a surface 306a of the conveyor, as in FIG. 5, for example. As above, the object 308 may be a cargo conveyance. Also as above, conveying systems 309a, 309b, shown in phantom, which may be separate or connected to each other, may be provided to move the radiation source 302 and detector 320 past the object 308 instead of moving the object.

The radiation source 302 comprises the linear accelerator 304, a bend magnet system 310, a target assembly 312 housing a target 313, and a collimator 315. The linear accelerator 304 is coupled to the bend magnet system 310 through a drift tube 314 and the bend magnet system is coupled to the target assembly 312 through a drift tube 316, all of which are under vacuum. The remaining structure of the target assembly 312 is the same as that of the target assemblies 142, 144 of FIG. 2 and is not further described here.

The linear accelerator 302 of FIG. 8 provides accelerated charged particles, such as electrons, through the drift tube 314 into the bend magnet system 310, such as one of the 270 degree achromats described above, which deflects the beams of accelerated charged particles towards a target 313 through the drift tube 316. In this example, the same bend magnet system 310 turns both beams of accelerated charged particles through a single orbit chamber, as discussed below.

Impact of the beam on the target 308 causes generation of radiation by the Bremsstrahlung effect, as is known in the art. The Bremsstrahlung X-ray radiation is emitted from the target 313 in all directions, with an angular distribution dependent upon the energy of the incident beam charged particles and the target, as is known in the art. The radiation emitted in the direction of the collimator 315 is collimated into the desired shape and emitted from the radiation source 302, toward the object 308. After interacting with the object 308, the radiation is detected by the detector 320, which may be a detector array. The detector 320 is coupled to a processor 322, which is coupled to a display 324, as above. The processor 324 or another processor may be coupled to the radiation source 304, the detector 320, and to the conveyor 306, 309a, 309b control their operation, as well. The detector 320 may be a detector array, for example. Additional circuitry, such as analog-to-digital circuitry, may be provided between the detectors 320 and the processor 124, as is known in the art. The processor 322 may be a logic circuit, such as an ASIC or FPGA, a programmable logic controller, or a microprocessor, for example.

Figure 9:
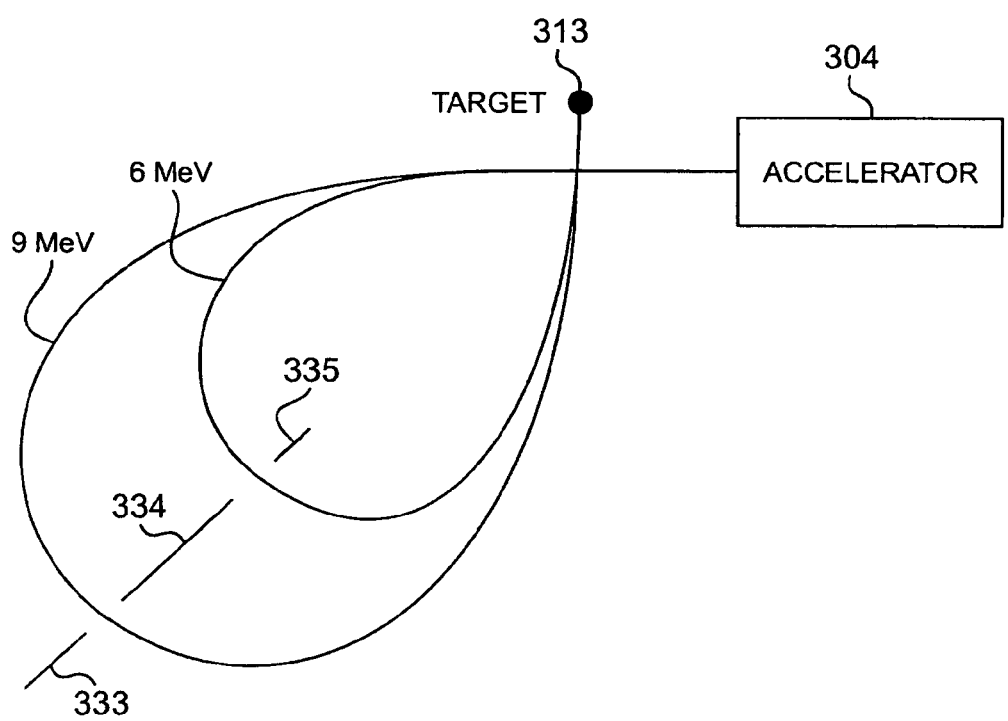
FIG. 9 is a schematic representation of two beam paths, one for a low energy accelerated electron beam and the other for a high energy accelerated electron beam, turned 270 degrees by the bend magnet system, in the embodiment of FIG. 8.

As mentioned above, in this example, the bend magnet system 310 turns both the higher and lower energy beams of accelerated charged particles toward the target 313 through the same orbit chamber. FIG. 9 is a schematic representation of two beam paths, one for a low, 6 MeV electron beam, and the other for a high, 9 MeV electron beam, turned 270 degrees by the bend magnet system 310 toward the target 313. Since the beam of charged particles accelerated to the higher energy, in this example 9 MeV, has greater kinetic energy, it must be turned over a wider radius than the lower energy beam, in this example 6 MeV, as is known in the art.

Also shown schematically in FIG. 9 are energy slits 333, 334, 335 that act as beam stops to intercept charged particles whose energies deviate from the desired acceleration energies (of 9 MeV and 6 MeV, for example), and whose radial displacements vary due to dispersion. The steps 333, 334, 335 define "energy slits" through which the charged particles of the desired energy ranges pass. For example, the energy slits 333, 334, 335 may be configured to remove charged particles with energies +/−3% of the desired central energy for each beam. In the case of the 9 MeV electron beam, electrons with energies greater than about 9.3 MeV and less than about 8.7 MeV may be removed, for example.

Figure 10:
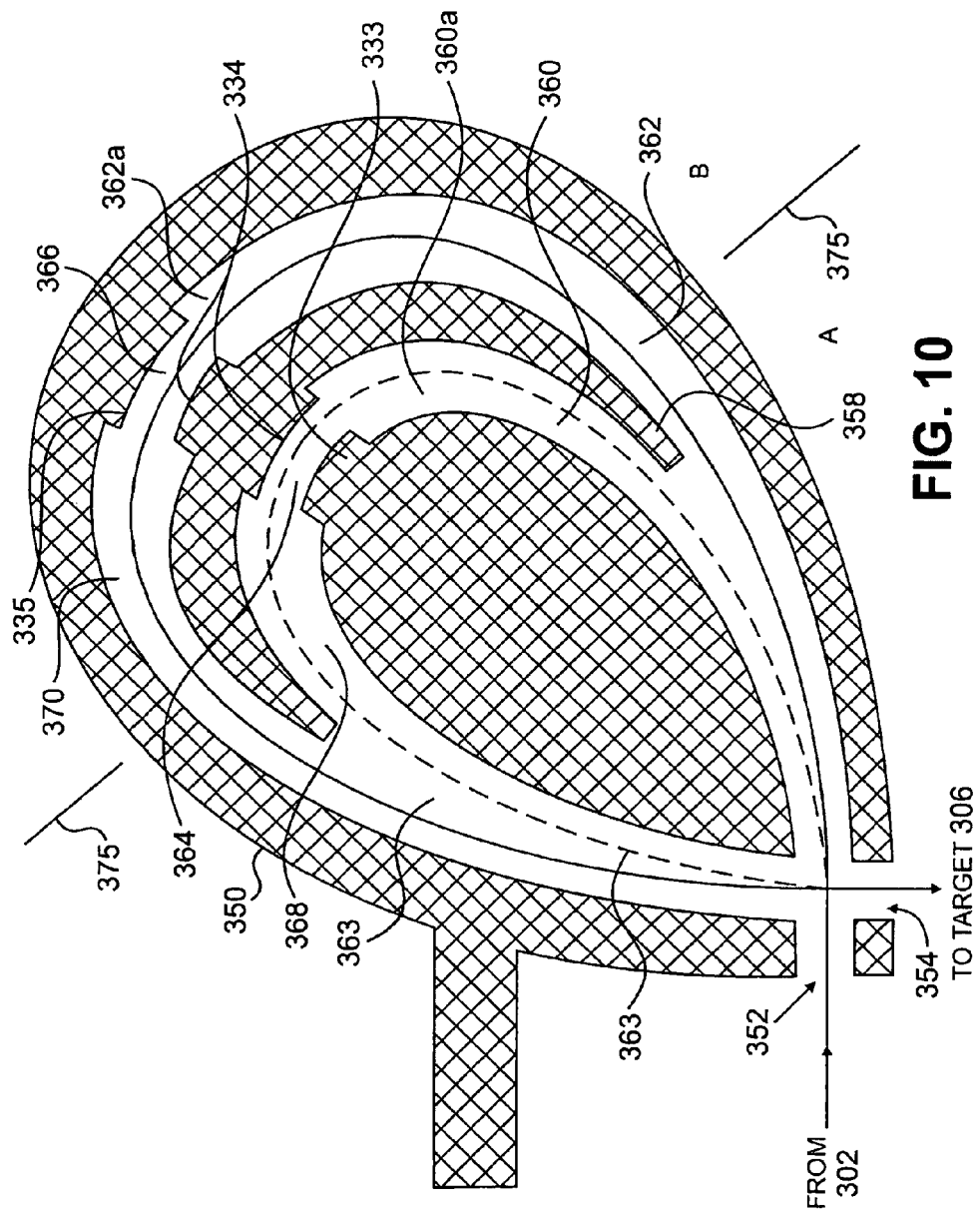
FIG. 10 is a cross section of an example of an orbit chamber that may be used with the high and low energy accelerated electron beams of FIG. 9.

FIG. 10 is an example of an orbit chamber 350 that may be used in the bend magnet system 310 to define a path for two different charged particle beams accelerated to two different energies. The orbit chamber 350 defines an inlet 352, an outlet 354, and a first passage 356 extending to a wall 358 that bifurcates the passage into two passages 360 and 362. The passages 360, 362 may merge into a single passage 363 near the outlet 354. The charged particle beam with the lower energy is bent over a smaller radius, through the passage 360, and the charged particle beam with the higher energy is bent over a larger radius, through the passage 362, as described above with respect to FIG. 9. The passages 360, 362 each curve around 270 degrees toward the outlet 354, as described above with respect to FIG. 4. As above, the orbit chamber 350 may comprise oxygen-free, electronic grade copper, which defines the passage 356. The inlet 352 to the orbit chamber 350 is coupled to the drift tube 314 and the output 354 of the orbit chamber is coupled to the drift tube 316.

Each passage 360, 362 may include a first, wider portion 360a, 362a extending from the inlet 352 to narrower choke sections 364, 366, respectively, followed by wider portions 368, 370 extending from the choke sections toward the outlet 354. The choke sections 364, 366 are defined by portions 333, 334, 335 of the orbit chamber that extend into the passages 360a, 362a. As discussed above, the choke sections 364, 366, which are optional, may be provided in each passage 360, 362 to provide beam stops to remove dispersed charged particles, such as electrons, with energies above and below the desired energy, as discussed above.

The orbit chamber 350 sits within a magnet system, as described above with respect to FIG. 3, or the other examples described above, for example. As above, two different magnetic fields may be applied to the orbit chamber 350 to achieve the desired curvature of the respective charged particle beams, also as described above. In FIG. 10, a line 375 represents a step or change in the magnetic fields between a low magnetic field in a region A through the orbit chamber 350, and a high magnetic field in a region B through the orbit chamber. The beam of charged particles is therefore first deflected by the low magnetic field in region A. When the step is crossed, the beam is subjected to a high magnetic field in region B and deflected a greater amount. When the beam returns to region A, the beam is again subjected to the low magnetic field. Due to the dispersion caused by the approximately achromatic stepped field angle, the two different beams charged particles may impact the target 313 up to several millimeters apart. The separation may be compensated for during analysis of the data so that the same or substantially the same scanning slices at the different energies may be compared, ratioed, etc. When the orbit chamber is arranged such that the separation is along the direction of movement of the object 308 (or the source 302 and the detector 320), the speed of movement of the object (source and detector) may compensate, at least in part, for the separation. Alternatively, a non-stepped, varying magnetic field may be used, such as an Enge magnet, which has less or no dispersion, as is also described above.

Figure 11:
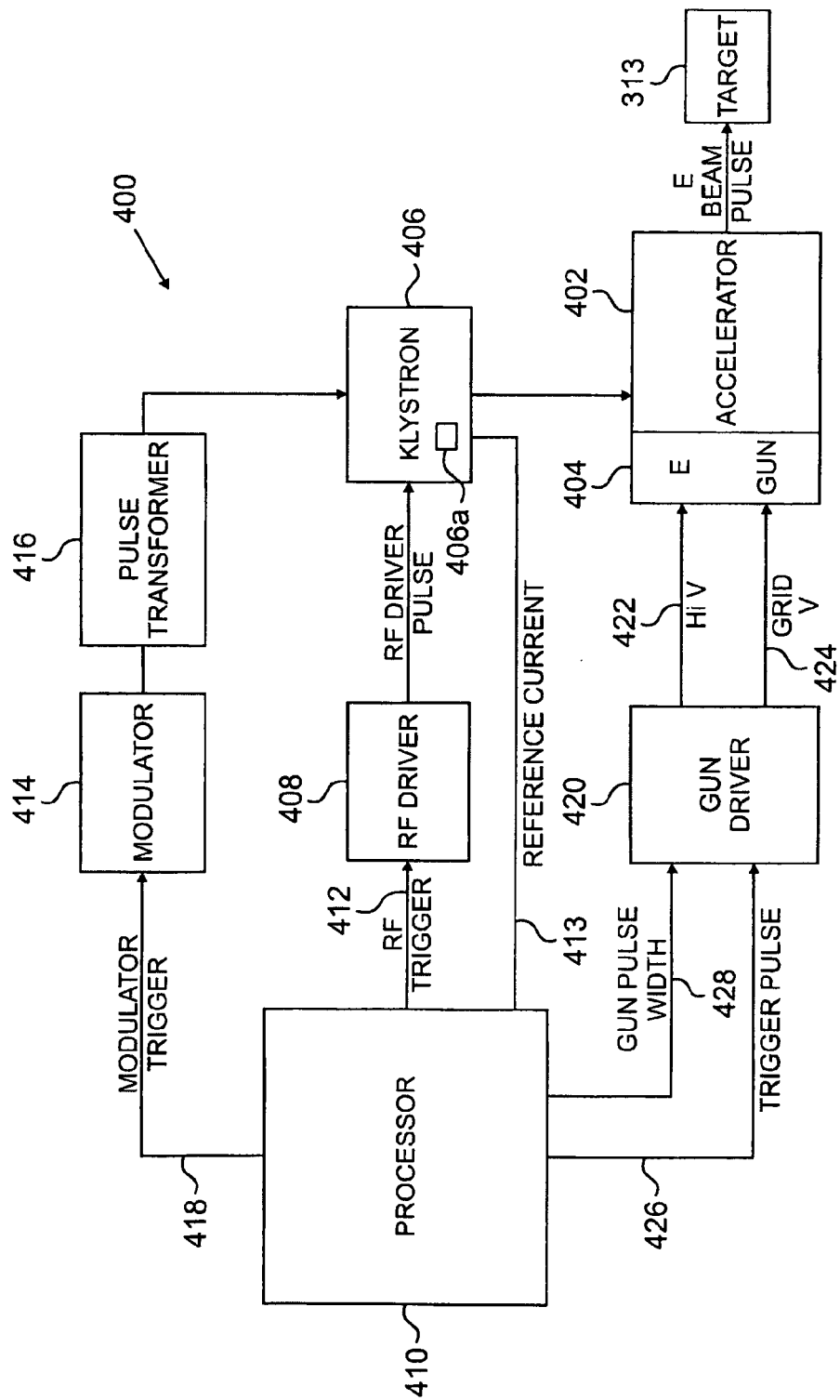
FIG. 11 is a schematic representation of an example of a radiation source that may be switched between accelerating charged particles, such as electrons, to different energies.

FIG. 11 is a schematic representation of an example of a radiation source 400 that may be switched between accelerating charged particles, such as electrons, to different energies, such as 9 MeV and 6 MeV, or 6 MeV and 1 MeV, for example, to generate radiation beams having energies of 9 MV and 6 MV, or 6 MV and 1 MV, respectively, for example. 9 MeV and 6 MeV, or 6 MeV and 1 MeV, the source 400 comprises an accelerator 402, such as a linear accelerator, and a source of charged particles 404, such as an electron gun, at an input end of the accelerator.

A microwave power source, such as a klystron 406, provides microwave or radio frequency (referred to generically as "rf") power to the accelerator 402. The klystron 406, which comprises a vacuum tube, is driven by an rf driver 408, as is known in the art. The rf driver 408 provides a programmable or selectable rf signal or pulse to the klystron 406 to modulate the rf field within the klystron. The signal may have a 20 Watt to 200 Watt peak power with a carrier frequency of 2856 MHz, 2998 MHz, or 9300 MHz, for example. The pulsed amplitude modulated signal may have a pulse width of 1 microseconds to 5 microseconds and a pulse repetition frequency of 50 Hz to 2000 Hz, with a duty factor of 0.004 to 0.005, for example.

A processor 410 provides a voltage trigger pulse to the rf driver 408 along line 412, to synchronize the rf driver output to the klystron 406. The processor 410 also provides inputs to the rf driver 408 to set the amplitude and frequency of the rf drive pulse provided along the line 412. A sensor 406a is provided in the klystron 406 to detect the current in the klystron. The processor 410 monitors the klystron current along a line 413. The processor 410, which may be the same as the processor 322 or another such processor, may be a logic circuit, such as an ASIC or FPGA, a programmable logic controller, or a microprocessor, for example. An automatic frequency control (not shown) may also be provided to provide closed logic feedback to the rf driver 408 to keep it locked on the accelerator resonance frequency, which can shift due to thermal transients and other accelerator perturbations. Automatic frequency control techniques are discussed in U.S. patent application Ser. No. 12/228,350, filed on Aug. 12, 2008 (U.S. Patent Publication No. US 2010/0038563 A1, published on Feb. 18, 2010), assigned to the assignee of the present invention, and incorporated by reference herein, for example.

The klystron 406 is also driven by a high voltage pulse modulator 414, which provides high power pulses to the klystron to establish the voltage on the klystron gun (not shown). The modulator 414 comprises a high voltage power supply and a pulse forming network (not shown), as is known in the art. An optional pulse transformer 416 may be provided to increase the voltage of the pulses provided to the klystron 406. For example, the modulator 414 may output 20 kV pulses that are increased to 120 kV by the pulse transformer 416. The processor 410 provides a modulator trigger pulse to the modulator 414 along line 418, to cause the modulator to start and stop generating each high voltage pulse. The voltage in the klystron 406, established by the voltage power pulses provided by the modulator 414, generates a high-current electron beam, which is subsequently modulated by the rf voltage pulses provided by the rf driver 408 to the klystron input cavity and by subsequent interaction with the klystron cavities, as is known in the art.

The accelerator electron gun 404 in this example is a triode gun, comprising a grid, an anode, and a cathode (not shown), as is known in the art. The electron gun 404 is driven by a gun driver 420, under the control of the processor 410. The grid of the gun 404 may be used to adjust the electron current from the gun to the accelerator 402, including disabling current. Changing the beam current changes the dose rate of the resulting radiation beams, and changes the beam energy by "beam loading," as is known in the art. The gun driver 420 provides a DC high voltage to the gun along line 422 and a lower voltage to the grid, along line 424. The DC voltage may be 3 kV to 30 kV, for example. The grid voltage (referenced to the chathode) may be −200 V to 400 V, for example. Typical beam perveance may be up to 0.3 μperv, depending on the grid setting. The processor 410 turns the gun driver 420 on and off via a gun trigger line 426 and defines the length of a pulse of electrons, along a gun pulse width line 428. The processor 410 also sets the high DC voltage to be provided to the electron gun 404, to the gun drive 420 along another line (not shown).

In this example, the high voltage signal along line 422 establishes a constant DC voltage between the anode and the cathode of the gun 404. The grid voltage is varied by providing three different voltage pulses to the grid, one voltage to turn the gun off, and two different voltages to define different beam currents during generation of each radiation beam, so that the dose rate of the radiation beams at the different energies are comparable.

In another example, the constant, high voltage defines one beam current, without providing a voltage pulse to the grid, and the other beam current is defined by providing a voltage pulse to the grid (with the constant high voltage also present). In another example, the amplitude of the high voltage pulse is varied or turned off by varying the amplitude of the high voltage pulse along line 422, as well as varying the grid voltage, along line 424.

The gun driver 420 comprises a fast circuit that changes the grid voltage levels on a pulse-to-pulse basis. The grid voltage levels may be changed on the order of 300 Hz to 400 Hz or faster, for example. The rate may be in kilohertz, for example. The processor 410 communicates with the gun driver 420 to set the level of the next voltage pulse to the grid, about 100-200 microseconds prior to the trigger of that pulse. The next voltage pulse may be the same or different, depending on the pattern of radiation to be generated.

To change the acceleration energy of the linear accelerator 402 from one nominal energy to another nominal energy, rf power provided to the accelerator 402 by the klystron 406 is varied, as is the voltage provided to the grid in the electron gun 404. The acceleration energy of the electrons and the energy of the generated radiation, are thereby changed.

Figure 12:
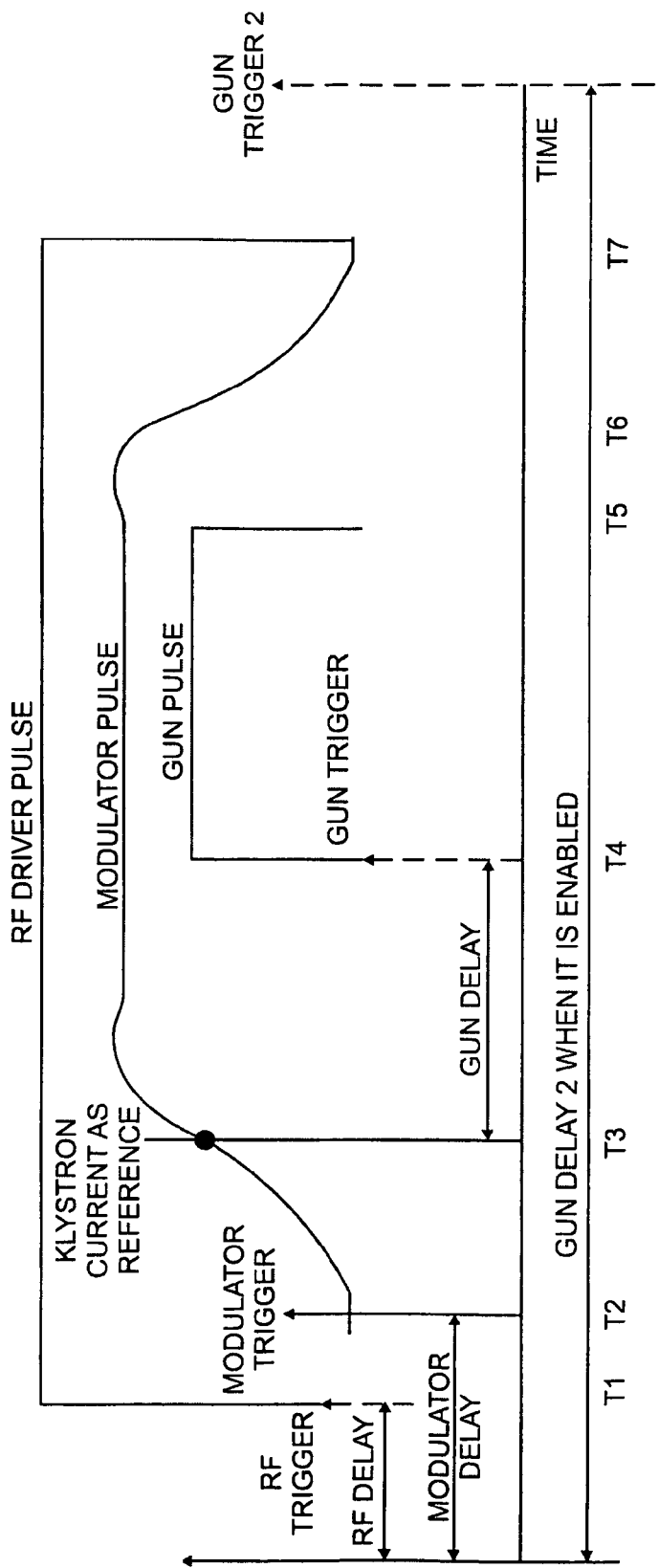
FIG. 12 is an example of a timing diagram for the radiation source of FIG. 11.

FIG. 12 is an example of a timing diagram for the radiation source 400 of FIG. 11, implemented by the processor 410 to switch the acceleration energy of the linear accelerator 402. After an rf delay of from about 0.1 to about 0.5 microseconds, the processor 410 triggers the rf trigger to the rf driver 408, along line 412 (see FIG. 9), at a time T1.

After a modulator delay of about 500 nanoseconds after the rf trigger is triggered, the processor 410 triggers the modulator trigger to the modulator 414, along line 418, at time T2.

Electrons are emitted into the accelerator 402 by the electron gun 404 when the klystron 406 is at the peak current, which takes place when the modulator pulse is at a peak voltage, in this example. Since it takes time for the voltage amplitude of the modulator 414 to rise to its peak value, such as 20 kV, for example, in this example the processor 410 triggers the gun trigger pulse along line 426 at a time 500-600 nanoseconds from the time a predetermined reference current is detected in the klystron 406 by the processor 410 (along line 413 in FIG. 6), to allow the modulator to reach the peak voltage. In this example, the gun delay is a predetermined time period starting from a time T3, when the klystron 406 current reaches a predetermined value, to a time T4. As discussed above, the processor 410 monitors the klystron current via the sensor 406 along the line 413, shown in FIG. 6.

The gun trigger pulse starts at the time T4 and ends at a time T5. The length of the gun trigger pulse in this example is from 1.0-4.5 microseconds. The start of the gun trigger pulse may be delayed to decrease the length of the beam pulse.

In this example, the modulator pulse starts to fall about 5.5 microseconds after being triggered, at a time T6. The rf pulse is turned off 6 microseconds after being triggered, at a time T7.

The process is then repeated to generate the next radiation pulse, by providing the same or a different rf voltage power pulse from the rf driver 408 to the klystron 406 and providing the same or different voltage pulse from the gun driver 420 to the electron gun 404, depending on whether the next radiation pulse to be generated by the radiation source 300 is to have the same or a different energy than the prior radiation pulse. A third, different rf voltage pulse may be provided by the rf driver 420 to the klystron 406 and a third, different voltage pulse may be provided from the gun driver 420 to the electron gun to accelerate charged particles to a third energy to generate radiation pulses to a third energy at a comparable dose rate as the first and second radiation pulses.

A desired radiation pulse pattern may be generated by providing a corresponding rf drive pulse pattern to the klystron 406 from the rf driver 408, and corresponding voltage pulse pattern to the grid from the gun driver 420, under the control of the processor 410. As discussed above, one example of a radiation pulse pattern is alternating high and low radiation pulses, each with comparable dose output levels for both the high and low energy radiation beams. Any pulse pattern may be implemented by the single radiation system, including the others discussed above.

In another example of driving an accelerator to accelerate electrons to two or more different energies to generate radiation at two or more respective energies, the rf output power of the klystron 406 may be varied by changing the high voltage on the klystron via the modulator 414, and keeping the output power of the rf driver 408 fixed. Instead of the klystron 406, the accelerator 402 may be driven by a magnetron.

Klystron and magnetron multi-energy radiation sources that may be used herein are also described in U.S. patent application Ser. No. 12/228,350, filed on Aug. 12, 2008 (U.S. Patent Publication No. US 2010/0038563 A1, published on Feb. 18, 2010), assigned to the assignee of the present invention, and incorporated by reference herein. A diode gun may be used instead of the triode gun 404, as is known in the art and is also described in U.S. patent application Ser. No. 12/228,350. The diode gun may be used with a high voltage pulsed modulator, for example. The high voltage pulse modulates the beam current directly. Alternatively, triode modulated-anode, or other electron emitters, may be used with a high voltage pulsed gun modulator.

Instead of the accelerator described above, an electrical energy switch and/or power variator may be used to accelerate charged particles at different energies in an interleaved fashion, as described in U.S. patent application Ser. No. 12/191,145, filed on Aug. 13, 2008 (U.S. Patent Publication No. US 2010/0039051 A1, published on Feb. 18, 2010), and U.S. patent application Ser. No. 11/475,433, filed on Jun. 26, 2006 (U.S. Pat. No. 7,786,823 B2, issued on Aug. 31, 2010), both of which were assigned to the assignee of the present invention and are incorporated by reference herein.

In another example, the support 306 may be a rotating platform and the radiation source 302, the detector 320, and/or the rotating platform may be movable vertically.

The dual energy test results may be analyzed, as discussed above. The radiation pulse sequence implemented by the single radiation source 400, as well as the conveyor speed, may also be changed, as described above, but in this case, the new radiation pulse sequence is generated by the same radiation system 400, under the control of the processor 410. In addition, the change in the radiation pulse sequence may include changing the dose rate at one or both radiation energies. The dose rate may be changed by changing the voltage provided to the grid of the electron gun 404 by the gun driver 420, or by other techniques described above, for example.

One of ordinary skill in the art will recognize that changes may be made to the embodiments described above without departing from the spirit and scope of the invention, which is defined by the claims, below.

We claim:

1. A method of examining contents of an object, comprising:
    accelerating first charged particles to a first energy;
    bending the first accelerated charged particles through a first passage toward a target by a magnet system;
    generating a first radiation beam having a second energy from impact of the first accelerated charged particles on the target;
    accelerating second charged particles to a third energy different than the first energy;
    bending the second accelerated charged particles through a second passage at least partially separate from the first passage, toward the target by the magnet system;
    generating a second radiation beam having a fourth energy different from the second energy from impact of the second accelerated charged particles on the target;
    scanning an object to be examined by the first radiation beam;
    detecting radiation after scanning the object by the first radiation beam;
    scanning an object to be examined by the second radiation beam; and
    detecting radiation after scanning the object by the second radiation beam.

2. The method of claim 1, comprising bending the first and second accelerated charged particles by 270 degrees.

3. The method of claim 1, comprising:
    generating a varying magnetic field by the magnet system to bend the first and second accelerated charged particle beams.

4. The method of claim 1, comprising:
    generating first and second, different magnetic fields by the magnet system to bend the first and second accelerated charged particle beams.

5. The method of claim 1, wherein the first and second passages extend at least partially through an orbit chamber defining the first and second passages, the method comprising:
    bending the first and second charged particle beams around respective, different, radii through the first and second passages, respectively, through the orbit chamber.

6. A radiation scanning system to examine contents of objects, the system comprising:
    a source of charged particles;
    a charged particle accelerator having an input coupled to the source of charged particles to receive the charged particles, and an output to allow accelerated charged particles to exit the accelerator along a first axis;
    the charged particle accelerator configured to generate a first beam of accelerated charged particles having a first energy and a second beam of accelerated charged particles having a second energy different than the first energy;
    a target positioned along a second axis different than the first axis;
    a magnet system along the first axis, configured to deflect the first and second accelerated charged particles through first and second at least partially separate passages, along the second axis, toward the target;
    wherein impact of the first charged particle beam on the target causes generation of a first radiation beam having a first energy and impact of the second accelerated charged particle beam on the target causes generation of a second radiation beam having a second energy different than the first energy;
    a support to support an object for scanning; and
    a detector to detect radiation after interacting with the object.

7. The radiation scanning system of claim 6, wherein the support comprises:
    a conveyor system to move the object through the first and second radiation beams, during scanning.

8. The radiation scanning system of claim 6, further comprising:
    a conveyor system to move the source and the detector past the object during scanning.

9. The radiation source of claim 6, wherein the radiation source is on a first side of the conveyor system and the detector is on a second side of the conveyor system opposite to the first side, to detect radiation transmitted through the object.

10. The radiation source of claim 6, wherein;
    the first and second axes are transverse; and
    the magnet system is configured to deflect the first and second charged particle beams 270 degrees, from the first axis to the second axis.

11. The radiation scanning system of claim 6, wherein the magnet system comprises:
    an orbit chamber defining;
    an inlet; and
    an outlet;
    wherein the first and second at least partially separate passages couple the inlet to the outlet, the first and second passages being configured to allow passage of the first accelerated charged particle beam and the second accelerated charged particle beam from the inlet to the outlet, respectively.

12. The radiation scanning system of claim 11, wherein the orbit chamber further defines:
    a wall separating a portion of the first passage from a portion of the second passage to define the first and second passages.

13. The radiation scanning system of claim 12, wherein:
    the wall extends from a portion of the first and second passages proximate the inlet to a portion of the first and second passages proximate the outlet.

14. The radiation scanning system of claim 13, wherein the orbit chamber defines a first, wider portion of each passage and a second narrower portion of each passage, the wider portion being upstream of the narrower portion, wherein a wall transverse to the passages defines a step between the first and second portions.

15. The system of claim 6, further comprising:
    a microwave power source to provide microwave power to the charged particle accelerator; and
    a processor coupled to the microwave power source;
    wherein the processor is configured to selectively cause the microwave power source to provide microwave power to the charged particle accelerator to selectively cause generation of the first beam of accelerated charged particles having the first energy and the second beam of accelerated charged particles having a second energy different than the first energy, to selectively cause generation of the first radiation beam or the second radiation beam.

16. The system of claim 15, wherein the processor is configured to:
implement a first, predetermined radiation pulse pattern; and
change the first predetermined radiation pulse pattern to a second, predetermined radiation pulse pattern different that the first predetermined radiation pulse pattern based, at least in part, on the radiation detected at at least one of the energies during scanning.

17. The system of claim 6, further comprising:
a conveyor to move at least one of the object, the radiation source, or the detector; and
a processor coupled to the conveyor, the processor configured to:
cause operation of the conveyor at a first speed during scanning; and
change the first speed to a second, different speed during scanning, based, at least in part, on the radiation detected at at least one of the energies during scanning.

18. The system of claim 6, wherein the magnet system is configured to generate a varying magnetic field.

19. The system of claim 6, wherein the magnet system is configured to generate first and second, different magnetic fields.

20. The method of claim 1, comprising:
bending the first charged particles and the second charged particles by a bend magnet.

21. The method of claim 20, comprising:
bending the first charged particles and the second charged particles by a stepped field bend magnet.

22. The method of claim 20, comprising:
bending the first charged particles and the second charged particles by an Enge magnet.

23. The system of claim 6, wherein the magnet system comprises a bend magnet.

24. The system of claim 23, wherein the bend magnet comprises a stepped field bend magnet.

25. The system of claim 23, wherein the bend magnet comprises an Enge magnet.

* * * * *